United States Patent
Hu et al.

(10) Patent No.: US 12,142,378 B2
(45) Date of Patent: Nov. 12, 2024

(54) DETECTING RECURRENCE OF A MEDICAL CONDITION

(71) Applicant: KONINKLIJKE PHILIPS N.V., Eindhoven (NL)

(72) Inventors: Yiyi Hu, Suzhou (CN); Yan Li, Shanghai (CN); Zuofeng Li, Shanghai (CN); Huichuan Sun, Shanghai (CN); Mao Hua Yang, Shanghai (CN); Jian Zhou, Shanghai (CN); Jia Fan, Shanghai (CN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 48 days.

(21) Appl. No.: 16/962,088

(22) PCT Filed: Jan. 16, 2019

(86) PCT No.: PCT/EP2019/050987
§ 371 (c)(1),
(2) Date: Jul. 14, 2020

(87) PCT Pub. No.: WO2019/141696
PCT Pub. Date: Jul. 25, 2019

(65) Prior Publication Data
US 2020/0342991 A1  Oct. 29, 2020

(30) Foreign Application Priority Data

Jan. 16, 2018  (WO) ................ PCT/CN2018/072811

(51) Int. Cl.
*G16H 50/20* (2018.01)
*A61B 5/00* (2006.01)
(Continued)

(52) U.S. Cl.
CPC ............... *G16H 50/20* (2018.01); *A61B 5/48* (2013.01); *G06F 16/243* (2019.01);
(Continued)

(58) Field of Classification Search
CPC ........ G16H 50/20; G16H 10/20; G16H 10/60; G16H 50/70; G16H 70/00; G16H 15/00;
(Continued)

(56) References Cited

U.S. PATENT DOCUMENTS

| | | | | |
|---|---|---|---|---|
| 2002/0107641 | A1* | 8/2002 | Schaeffer | G16H 70/60 702/19 |
| 2013/0006672 | A1* | 1/2013 | Dang | G06Q 30/02 705/2 |

(Continued)

FOREIGN PATENT DOCUMENTS

WO  2012122122 A1  9/2012

OTHER PUBLICATIONS

International Search Report and Written Opinion for International Application No. PCT/EP2019/050987, filed Jan. 16, 2019, 15 pages.
(Continued)

*Primary Examiner* — Jonathan Ng
*Assistant Examiner* — Benjamin L. Hanks (57) ABSTRACT

Presented are concepts for detecting recurrence of a medical condition in a subject previously treated for the medical condition. One such concept comprises, using natural language processing, extracting information from a data set comprising information relating to the subject prior to and/or during the subject's previous treatment for the medical condition. The extracted information is reformulated into structured data based on a standardized model. A data retrieval request comprising a structured query adhering to
(Continued)

a template is obtained and, based on the structured query of the data retrieval request, data is retrieved from the structured data.

13 Claims, 4 Drawing Sheets

(51) Int. Cl.
*G06F 16/242* (2019.01)
*G06F 16/25* (2019.01)
*G06F 40/20* (2020.01)
*G06F 40/40* (2020.01)
*G16H 10/20* (2018.01)
*G16H 10/60* (2018.01)
*G16H 50/70* (2018.01)
*G16H 70/00* (2018.01)

(52) U.S. Cl.
CPC ............ *G06F 16/258* (2019.01); *G06F 40/20* (2020.01); *G06F 40/40* (2020.01); *G16H 10/20* (2018.01); *G16H 10/60* (2018.01); *G16H 50/70* (2018.01); *G16H 70/00* (2018.01)

(58) Field of Classification Search
CPC ......... G16H 50/50; A61B 5/48; G06F 16/243; G06F 16/258; G06F 40/20; G06F 40/40
See application file for complete search history.

(56) References Cited

U.S. PATENT DOCUMENTS

| | | |
|---|---|---|
| 2014/0181128 A1 | 6/2014 | Riskin et al. |
| 2016/0098533 A1* | 4/2016 | Jackson ................ G16H 50/70 |
| | | 705/3 |
| 2016/0210427 A1* | 7/2016 | Mynhier ................ G16H 10/60 |

OTHER PUBLICATIONS

Carrell, et a., "Using Natural Language Processing to Improve Efficiency of Manual Chart Abstraction in Research: The Case of Breast Cancer Recurrence", American Journal of Epidemiology, Jan. 30, 2014, vol. 179, No. 6, pp. 749-758.

Hochheiser, et al., "An information model for computable cancer phenotypes", BMC Medical Informatics and Decision Making 2016, 16:121, pp. 1-15.

Geraci, et al., "Applying deep neural networks to unstructured text notes in electronic medical records for phenotyping youth depression", Evid Based Mental Health, Aug. 2017, vol. 20, No. 3, pp. 83-87.

Ritzwoller, et al., "Development, Validation, and Dissemination of a Breast Cancer Recurrence Detection and Timing Informatics Algorithm", Journal of the National Cancer Institute, 2018, 110(3), pp. 273-281.

\* cited by examiner

DETECTING RECURRENCE OF A MEDICAL CONDITION

RELATED APPLICATIONS

This application is the U.S. National Phase application under 35 U.S.C. § 371 of International Application No. PCT/EP2019/050987, filed on Jan. 16, 2019, which claims priority to International Application No. PCT/CN2018/072811, filed Jan. 16, 2018. These applications are hereby incorporated by reference herein.

FIELD OF THE INVENTION

This invention relates to the field of Clinical Decision Support (CDS), and more particularly to detecting recurrence of a medical condition in a subject.

BACKGROUND OF THE INVENTION

Detecting the recurrence of a medical condition (e.g. disease or illness) is a common but important task for medical care of a subject and clinical research.

Typically, monitoring of subject previously treated for a medical condition is conducted manually (e.g. via visits to/from a medical professional, or by calling a subject (or the subjects carer) by phone to seek information). This approach has two main issues: (i) subjects typically have limited medical knowledge and/or awareness, and thus fail to provide accurate information or feedbacks; and (ii) standardized and/or well-defined procedures are required for a medical professional conducting the monitoring to ensure consistency and accuracy of collected information. In an attempt to improve such subject monitoring, medical professional (e.g. doctors, physicians, consultants, and the like) may review a large amount of clinical data, records, medical documents, notes, clinical reports, test results, etc. for a subject so as to identify and collate phenotypes as indicators of recurrence. To assist in forming a conclusions, diagnosis guidelines may be used. Diagnosis guidelines may include a set of phenotypes and decision rules/logic for assisting the identification of a subject's recurrence status.

However, with recent increasing demand for clinical trials and large growth in the amount of available clinical research data, both frequency and work load of subject follow-up is growing rapidly. Conduct the abovementioned manual processes for patient monitoring is therefore becoming more inefficient and labor intensive.

Accordingly, there is a desire to improve processes for detecting the recurrence of a medical condition, for example through the use of automation and/or the assistance of processing system. However, this faces the problem that medical guidelines, documents, data and the like are typically not standardized or formally documented. Such information may also change over time with the evolution of clinical knowledge. Furthermore, it can be difficult and computationally expensive to collect phenotypes from different medical documents and transform complex decision rules into accurate and trusted implementations. It can also be difficult to implement updates and maintain data and/or processes whenever there are changes in medical guidelines.

SUMMARY OF THE INVENTION

The invention is defined by the claims.

The invention aims to at least partly fulfil the aforementioned needs. To this end, the invention provides devices, systems and methods as defined in the independent claims. The dependent claims provide advantageous embodiments.

According to the invention, there is provided a method for detecting recurrence of a medical condition in a subject previously treated for the medical condition. The method comprises: using natural language processing, extracting information from a data set comprising information relating to the subject prior to and/or during the subject's previous treatment for the medical condition; reformulating the extracted information into structured data based on a standardized model; obtaining a data retrieval request comprising a structured query adhering to a template; and retrieving data from the structured data based on the structured query of the data retrieval request.

There is proposed a recurrence detection framework which is efficient, scalable and generalizable. In particular, there is provided a recurrence detection workflow that need not be restricted to particular medical condition or illness. Embodiments therefore need not be restricted to liver cancer recurrence detection for example.

For medical professionals, doctors, consultants, and the like, the proposed concept(s) may provide convenience in both accessing desired data and defining decision rules or guidelines. Also, for developers, the proposed concept(s) may enable easy implementation and a high-level of transferability.

There is proposed an approach to recurrence detection that merges phenotype results extracted using NLPs.

When compared with conventional recurrence detection systems, proposed embodiments may provide the following advantages: (i) extensible data extraction and flexible data aggregation for decision support; (ii) simplification of a decision-making process; and (iii) improved ability to be generalizability to a range of diseases (including various forms of cancer).

Embodiments may thus propose the reformulation of data (extracted using NLP) into structured data based on a standardized model. Structured queries (e.g. queries adhering to a template) may then be used to retrieve data from the structured data, thereby facilitating the provision of information in a manner which may be simple, intuitive and supports identification of disease recurrence. Retrospective study of clinical data and/or medical information may thus be facilitated by embodiments. For instance, a subject's follow-up results may provide important metrics and information for evaluating conducted treatment, and this may therefore be important for selecting future treatment. Proposed embodiment may thus provide assistance in carrying out retrospective studies. Accordingly, there may be provided concepts for assisting the provision of subject-specific clinical information that enables improved CDS.

Proposed concepts may thus increase the clinical value of information by enabling subject-specific clinical information to be provided in an automated manner. This may support assessment, enable improved focus on a disease recurrence identification, and/or support clinical planning. Improved CDS may therefore be facilitated by proposed concepts.

According to embodiment, it is proposed to separate data extraction from data acquisition. Each of a plurality of NLP processes may specify as many phenotypes as possible that it has the capability to extract. The results from the NLP processes can then be provided via the same interface for storage. The data set(s) from which data may be acquired may therefore comprise unstructured or semi-structured data.

Since data of interest can depend on a user, it is proposed to employ a standard for both data storage and acquisition. Put another way, employing different NLP processes may place demands on data storage and queries (e.g. because the different NLP process may produce results in diversified formats) and the use of a standard is proposed. In particular, some proposed embodiments employ the Fast Healthcare Interoperability Resources (FHIR) standard. FHIR is a standard created by the Health Level Seven International (HL7) health-care standards organization. FHIR offers standard description of data formats and elements (also known as resources) and Application Programming Interface (API) to exchange electronic clinical data (e.g. health records) among different system components and systems.

In some embodiments, instead of using FHIR for data exchange between systems, it is firstly used in combination with NLP to maintain extracted phenotype values and then it is later used with a Domain Specific Template (DST) for data query and aggregation. For instance, it is proposed to firstly use a FHIR resource wrapper interface, which transforms NLP results to a standardized FHIR data storage format. More specifically, Questionnaire (Q) and Questionnaire Response (QR) resources can be employed in proposed embodiment. A Questionnaire defines a set of questions (usually nested) to be answered, while a Questionnaire Response responds to a Questionnaire by filling answers to the questions of the Questionnaire. Such a proposal thus abstracts a process of phenotype extraction as an NLP process answering a Questionnaire of phenotypes whose values awaits extraction. Each of a plurality of NLP processes can maintain its own associated Questionnaire, whilst the NLP processes all interact with the same FHIR interface to provide extraction outputs as answers in a corresponding QR. Secondly, in order to fetch stored phenotype values, another FHIR interface is proposed that provides query APIs for phenotype values in a Questionnaire Response.

Accordingly, it will be understood that the proposed framework may be capable of integrating extraction results returned from a plurality of different NLP processes, including results produced by external NLP processes. In this way, a user (such as an oncologist or other medical professional) can leverage results produced by different NLP tools in order to obtain more information and make more-informed decisions. Thus, the proposed framework can be scalable and continuously improve and/or increase its capabilities. A user may also actively re-define or adjust required data, as well as the way data is aggregated without needing to wait for updates (as long as such desired data is extractable using the available NLP processes).

By way of example, the step of reformulating the extracted information into structured data may comprise: organizing the extracted information based on a questionnaire format and a format of the extracted data. For instance, in proposed embodiments, the step of reformulating the extracted information into structured data may comprise: using a resource wrapper interface to transform the extracted information to a standardized data format, wherein the standardized data format is defined by the standardized model. The format may comprise a template of questionnaire and questionnaire response resources in FHIR for example. These may contain a standardized structure to follow, such as one or more nested groups of questions and answers. In this way, proposed embodiments may take advantage of standardized structures which allow flexible and/or complicated definitions of data items to be extracted, and such structures may employ nested structures for example. Taking such an approach may be beneficial for 3rd party NLPs by enabling the definition of their own data items in a certain structure that will satisfy end usage. Also using questionnaire and questionnaire response resources may increase data interoperability with other FHIR data resources.

As mentioned above, the employed standard may be FHIR. Hence, the resource wrapper interface may comprise a Fast Healthcare Interoperability Resources, FHIR, resource wrapper interface, and the standardized model may comprise a FHIR model.

In an embodiment, the structured query may comprise at least one of: an identifier of a subject; an identifier of a document; a phenotype; a definition of a permissible phenotype; a decision rule; and an identifier of a function. By way of example, the identifier of a function may be used when a user want to re-use and invoke a previously implemented function. Conversely, if a user wants to re-create a function, he/she may instead create a new function (e.g. via a define-get process as described below).

In proposed embodiments, the template may comprise a definition of permissible phenotypes and decision logic. For instance, in order to aggregate phenotypes extracted by NLP modules and apply decision rules to identify recurrence in an efficient way, use of a Domain Specific Template (DST) is proposed. A DST may encode information required for computation, e.g. phenotypes as well as decision logic required by a recurrence detection task, and this may be provided in in a single human-readable file (e.g. JSON).

In particular, the inventors propose a process referred to a "name-define-get" in a DST, and by employing this process users can obtain required information (in FHIR QR format), phenotypes and implement decision rules with reduced costs. For example, a user can retrieve a subject's medical records and extracted phenotypes simply by naming them in a DST file, without needing to know details about how they were extracted, stored and fetched—This is referred to as "name-get". In addition, a user is provided with freedom to define new phenotypes according to his/her needs based on existing phenotypes—This is referred to as "define-get". Also, besides phenotypes, decision rules can be implemented by creating DST functions and invoked 'on-the-fly' via define-get. Similarly, a function can employ the name-get process and thus be invoked by reference to its name. The proposed framework can automatically save phenotypes and functions when a name is assigned to them during definition, such that they become accessible via the name-get process later for reuse purpose.

In embodiments, the step of retrieving may comprise: identifying a pair of connected data elements of the structured data, each of the pair of connected data elements comprising respective phenotypes; based on the respective phenotypes of the connected elements, determining if the connected data elements indicate recurrence; and retrieving at least one of the connected data elements based on whether it is determined that recurrence is indicated. For example, an execution tree may be generated based on a DST file. The execution tree may be a static tree skeleton (e.g. a pile of phenotypes and function names/definitions) and does not compute anything until executed. During execution, named phenotypes are fetched automatically (e.g. via a FHIR query interface) and gathered, while newly-defined phenotypes are derived from already fetched phenotypes. A decision path may be computed on-the-fly by traversing and executing each node in the tree structure.

To accomplish a recurrence detection task, subject phenotypes as indicators can be collected and aggregated as an input for a decision process based on diagnostic guidelines, thereby enabling a conclusion on recurrence status to be determined.

According to proposed concepts, NLP capabilities may be improved by employing first and second FHIR interfaces to standardize storage and query process of extracted phenotypes. Further, a two-phase match-decide (M-D) process is proposed which may reduce the complexity of a recurrence detection process, and such a M-D process can be implemented in executable JSON file (e.g. equivalent to a DST file). By employing such concepts, implementation and/or modification of the recurrence detection process need only require the editing of a file editing while the proposed framework delegates implementation details away from a user. Embodiment may therefore require significantly less effort to implement and/or may be easy to adapt to changes.

According to another aspect, there may be provided a computer program product downloadable from a communications network and/or stored on a computer readable medium and/or microprocessor-executable medium wherein the computer program product comprises computer program code instructions, which when executed by at least one processor, implement a method according to an embodiment.

According to another aspect, there may be provided a system for detecting recurrence of a medical condition in a subject previously treated for the medical condition. The system comprises: a natural language processing arrangement adapted to extract information from a data set comprising information relating to the subject prior to and/or during the subject's previous treatment for the medical condition; a first interface component adapted to reformulate the extracted information into structured data based on a standardized model; a second interface component adapted to obtain a data retrieval request comprising a structured query adhering to a template; and a data retrieval component adapted to retrieve data from the structured data based on the structured query of the data retrieval request.

BRIEF DESCRIPTION OF THE DRAWINGS

Examples of the invention will now be described in detail with reference to the accompanying drawings, in which.

DETAILED DESCRIPTION OF THE EMBODIMENTS

Illustrative embodiments may be utilized for detecting the recurrence of many different types of diseases, medical conditions or illnesses. In order to provide a context for the description of elements and functionality of the illustrative embodiments, the Figures are provided hereafter as example environments in which aspects of the illustrative embodiments may be implemented. It should therefore be appreciated the Figures are only examples and are not intended to assert or imply any limitation with regard to the environments or systems in which aspects or embodiments of the present invention may be implemented.

Embodiments of the present invention are directed toward enabling a disease recurrence detection framework which is efficient, scalable and generalizable. Examples of user may therefore include medical professionals, doctors, consultants, and the like.

According to proposed concepts, there may be provided methods or systems for accessing desired clinical data and defining decision rules or guidelines. Such a concept proposes an approach to recurrence detection which merges phenotype results extracted using NLPs. Embodiments may, for example, comprise the reformulation of data (e.g. extracted using NLP processes) into structured data based on a standardized model. Structured queries (e.g. queries adhering to a template) can then be used to retrieve data from the structured data, thereby facilitating the provision of information in a manner which may be simple, intuitive and supports identification of disease recurrence. Improved CDS may therefore be provided by proposed embodiments.

Illustrative embodiments may be utilized in many different types of clinical, medical or patient-related environments, such as a hospital, doctor's office, ward, care home, person's home, etc. In order to provide a context for the description of elements and functionality of the illustrative embodiments, the Figures are provided hereafter as examples of how aspects of the illustrative embodiments may be implemented. It should therefore be appreciated the Figures are only examples and are not intended to assert or imply any limitation with regard to the environments, systems or methods in which aspects or embodiments of the present invention may be implemented.

Figure 1:
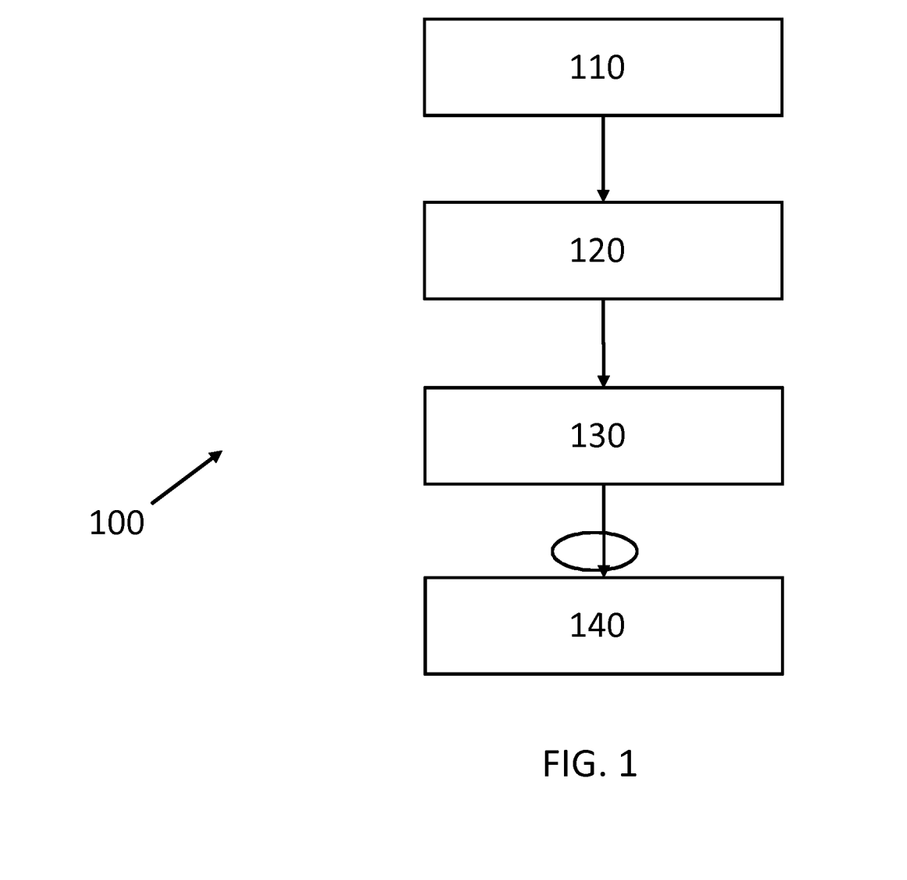
FIG. 1 is an exemplary flow diagram of a method for detecting recurrence of a medical condition in a subject according to an embodiment.

Referring now to FIG. 1, there is depicted an exemplary flow diagram of a method 100 for detecting recurrence of a medical condition in a subject according to an embodiment.

The method begins with step 110 of extracting, using NLP, information from a data set comprising information relating to the subject prior to and/or during the subject's previous treatment for the medical condition. Here, the data set comprises unstructured or semi-structured data. In other words, the data set comprises various forms and types of data that does not adhere to a single, defined storage structure.

Next, in step 120, the extracted information is reformulated into structured data based on a standardized model. Here, reformulating the extracted information into structured data comprises using a resource wrapper interface to transform the extracted information to a standardized data format, wherein the standardized data format is defined by the standardized model. For example, in this embodiment, the resource wrapper interface comprises a Fast Healthcare Interoperability Resources, FHIR, resource wrapper interface, and the standardized model comprises a FHIR model. In particular, questionnaire and questionnaire response resources available in FHIR are used to organize the extracted information, thus enabling a standardized structure to be followed.

The method then proceeds to step 130 wherein a data retrieval request is obtained. The obtained data retrieval request comprises a structured query adhering to a template which defines permissible phenotypes and decision logic. In particular, the structured query comprises at least one of: an identifier of a subject; an identifier of a document; a phenotype; a definition of a permissible phenotype; a decision rule; and an identifier of a function.

Based on the structured query of the data retrieval request, data is then retrieved from the structured data in step 140.

Here, the step 140 of retrieving comprises: identifying a pair of connected data elements of the structured data, each of the pair of connected data elements comprising respective phenotypes. Based on the respective phenotypes of the connected elements, it is determined if the connected data elements indicate recurrence. If recurrence is indicated, at least one of the connected data elements is retrieved.

From the above-described method of FIG. 1, it will be understood that phenotype results are extracted using NLPs and then merged to provide structured data based on a standardized model. Structured queries (e.g. queries adhering to a template) can then be used to retrieve data from the structured data, thereby facilitating the provision of information in a manner which is simple and intuitive. Retrospective study of clinical data and/or medical information is therefore facilitated, and this may support identification of disease recurrence.

Figure 2:
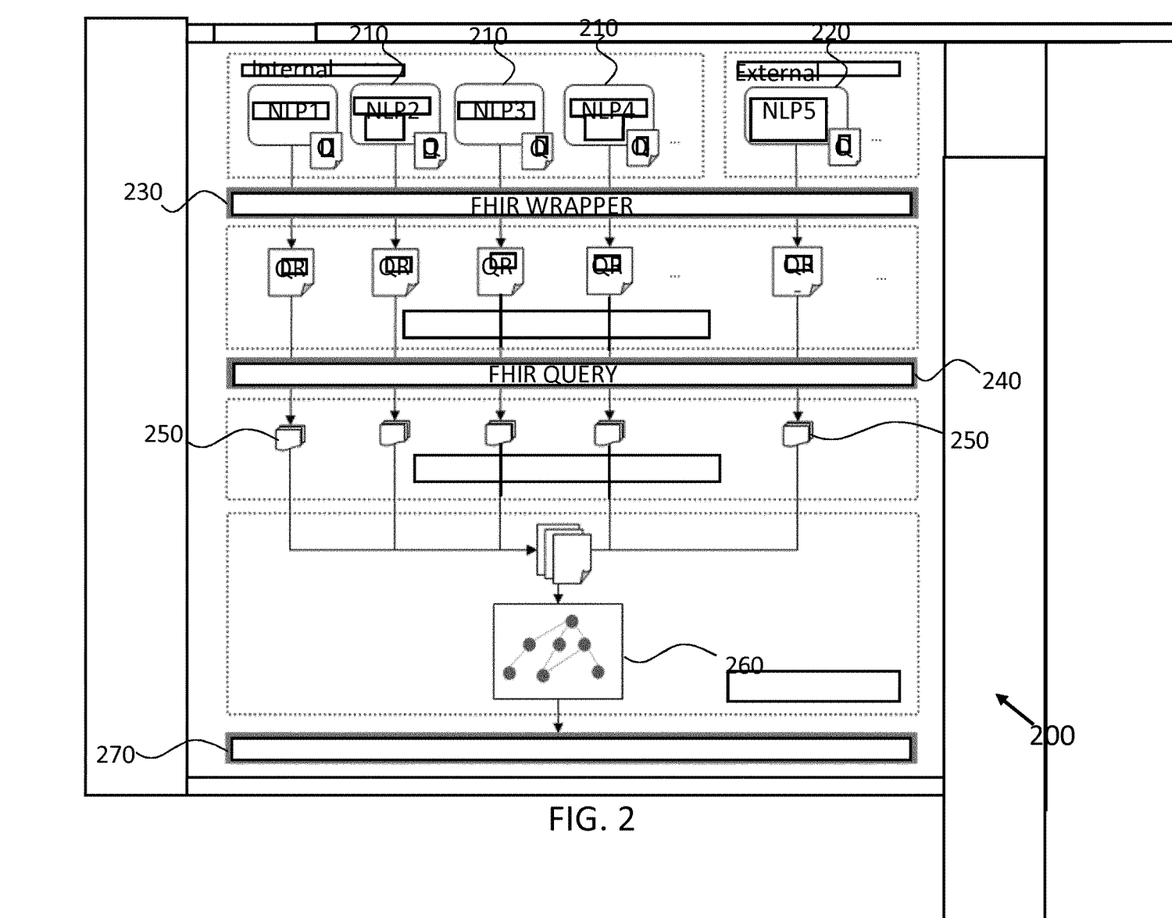
FIG. 2 depicts a system for detecting recurrence of a medical condition in a subject according to an embodiment.

Turning now to FIG. 2, there is depicted a system 200 for detecting recurrence of a medical condition in a subject according to an embodiment.

In the system 200, data extraction is separated from data acquisition. First to fourth Internal NLP modules 210 are provided, namely NLP1 through NLP4, along with a first external NLP module 220, namely NLP5. Each NLP module is able to specify as many phenotypes as possible that it has the capability to extract. All of the NLP modules 210,220 provide extracted results (in response to a questions Q) to a FHIR wrapper interface 230.

The HL7 FHIR standard is used for both data storage and acquisition of results. The system 200 is therefore capable of integrating extraction results returned by multiple modules 210,220, including those produced by the external NLP module 220. In this way, a user is provided with the ability to leverage results produced by different NLP module in order to achieve better results. Also, the system is scalable so that it can continuously build up its capability. Furthermore, a user may actively change data required as well as the way it is aggregated without waiting for system updates, as long as the desired data is extractable by the NLP modules 210, 220 that are employed by the system.

Employing different NLP modules 210,220 means that extracted results may be provided in diverse formats. To address this, a FHIR wrapper interface 230 is employed so as to employ a standard description of data formats and elements (also known as resources). Thus, in the proposed system, instead of using FHIR for data exchange between systems, it is used in combination with NLP modules to obtain the extracted phenotype values. In particular, the FHIR resource wrapper interface 230 transforms NLP results to a standardized FHIR data storage format. More specifically, in the embodiment of FIG. 2, Questionnaire (Q) and Questionnaire Response (QR) resources are used. A Q defines a set of questions (usually nested) to be answered, while QR responds to a Q by filling answers to the appropriate questions. The embodiment thus abstracts the process of phenotype extraction as a process of NLP module answering a questionnaire of phenotypes whose values awaits extraction. Each NLP module 210,220 maintains its own respective Q, but interacts with the single FHIR wrapper interface 230 to wrap extraction results as answers in a corresponding QR.

To fetch stored phenotype values, the proposed embodiment employs a second FHIR interface, namely a FHIR query interface 240, which is adapted to provide query APIs for phenotype values in a QR.

To aggregate phenotypes 250 extracted by NLP modules and apply decision rules to identify recurrence in an efficient way, the embodiment employs a domain specific template (DST). A DST encodes information required for computation as well as decision logic required by a recurrence detection task, and thus information may be provided in a single human-readable file (e.g. a JSON file).

In particular, the inventors have designed a mechanism called 'name-define-get' in a DST with which users of an embodiment are able to collect required documents (in FHIR QR format) and phenotypes and implement decision rules with minimized costs. Users may thus retrieve subject records and extracted phenotypes by simply naming them in a DST file (e.g. without caring about details of how they were extracted, stored and/or fetched). This is referred to a 'name-get'. Further, embodiments provide a user with freedom to define new phenotypes according to needs based on existing phenotypes. This is referred to as 'define-get'.

Also, besides phenotypes, decision rules can be implemented by creating DST functions and invoking them on-the-fly via the 'define-get' mechanism. Similarly, functions can defined using the 'name-get' mechanism and invoked by referencing their name.

The proposed system can automatically save phenotypes and functions when a name is assigned to them during definition, such that they become accessible via the name-get mechanism for reuse purposes.

When communicating results to users, extensive technical details may not be necessary. Thus, the decision DST is adapted to minimize a gap between guidelines and implementations. It may be more readable and more intuitive to understand so that even medical professionals with limited computing knowledge are able to use a DST.

The embodiment of FIG. 2 employs a decision DST 260 which comprises a representation of decision tree. Each node of the tree is an atomic DST unit, which comprises a set of phenotypes (either named or defined), a logic gate function and a set of return functions. Here, the logic gate function drive a decision path to formulate a conclusion.

During execution, named phenotypes are fetched automatically via the FHIR query interface 240 and gathered, while newly-defined phenotypes are derived from already fetched phenotypes. A decision path is computed on-the-fly by traversing and executing each node in the tree structure 260 using a tree executer 270.

By way of further description, various exemplary aspects of the proposed system of FIG. 2 will now be described in more detail as follows:

Match and Decide (M-D)

To cater for complexity of decision rules and any missing information, the inventors propose a 2-phase process referred to as 'Match-Decide' (M-D) and which can be generalized for other recurrence detection tasks. The M-phase links two causally connected clinical documents, and outputs linked documents in pairs. For instance, a surgical operation note may be linked to an earlier imaging diagnostic report which indicated a relapsed nodule on liver and as a result, the surgery was performed.

The M-phase helps to identify missing patient records by pairing unlinked documents with an empty value. Then, given these pairs as input, the D-phase employs decision trees to decide whether the input document(s) can indicate recurrence based on phenotypes contained in them. Finally, if an output from a decision tree is non-negative, a recurrence time is marked by using a timestamp containing the relevant document.

To enable M-D process, pre-define operators can be defined as enabler functions as described in Table 1 below:

TABLE 1

| Operators | Description | Example |
| --- | --- | --- |
| MATCH[S1, S2] | Find causally connected documents between two sets S1 and S2. | MATCH[{Opn}, {img}] matches operation note and imaging report which shared causal connection among a pile of operation notes and |
| FILTER[X, C]/ FILTER[X, P] | Filter X for which condition C holds. It can also filter input X by matching against pattern P. In this way, the system is able to deal with different missing cases separately. | FILTER[X, <TYPE_OPN, TYPE_IMG>] matches pairs whose types are operation note and imaging report, while FILTER[X, <TYPE_OPN, NULL>] and FILTER[X, <NULL, TYPE_IMG>] matched imaging diagnose missing and imaging report with treatment missing respectively. |
| DT[X] | Calls the decision tree process of corresponding input document X. | DT[opn] calls a decision tree for operation notes while DT[img] calls a decision tree for imaging reports. |
| MARK[X, TIME[Y]] | A combined operator marks the timestamp of X with timestamp of Y. | MARK[status, TIME[img]] and MARK[status, TIME[opn]] marks the output recurrence status using timestamp of imaging report and operation notes respectively. |

With the operators defined above in Table 1, a M-D process for operation notes can be created. For example: step (i) may comprise "MATCH[{Opn}, {img}]" to match an operation note and imaging report which have a shared causal connection amongst a collection of returned operation notes; step (ii) may then comprise "FILTER[{(opn, img)}, <TYPE_OPN, TYPE_IMG>]" to match pairs whose types are operation note and imaging report. In this way, the filtering is carried out amongst a set of pairs. Such filtering should result in operation notes and imaging report pairs without NULL cases (either missing operation note or missing imaging report). Missing cases are matched as: FILTER[{opn, _}, <TYPE_OPN, NULL>] and FILTER[{_, img}, <NULL, TYPE_IMG>]. Step (iii) may then comprise "DT[opn]" to call a decision tree for the filtered operation notes; and step (iv) may then comprise "MARK[status, TIME[img]]" to mark the output recurrence based on the result from step (iii).

Decision Trees

At each node of a decision tree is a gate function, which drives a decision path until leaf nodes are reached. As output values at leaf nodes, it is proposed to use: "Y" to denote detection of a recurrence; "N" to denote detection of no recurrence; "SUSP" to denoted an uncertain and/or suspicious detection; and "CHK" as a warning for data checking. Thus, "CHK" is used for situations where there is unreasonable missing of data, which may require manual checking e.g. a missing pathology report of a surgical operation.

Using such values, pre-defined logic gate functions may be provided as detailed in Table 2 below:

TABLE 2

| Gate Function | Description | Example |
| --- | --- | --- |
| IS[X, Y]n | True if Y is a hypernym of X. | IS[opn_type, intervention] checks if the operation note type is intervention. As an example, when 'Opn_Type = TACE', in which 'TACE' is an intervention procedure, the function gives true. |
| IN[X, S] | True if X is in a set S. | As shown in [fig], IN[opn_type, {RFA, PEI, MWA}] returns true if the procedure type is one of radiofrequency ablation (RFA), percutaneous ethanol injection (PEI) or micro wave ablation (WMA). In imaging report example ([fig]), IN is used to check if a diagnosis of recurrence appears in conclusion part of the report. |
| EXIST[X] | Returns true if X exists. | In [fig], EXIST[<opn, pathology>] means whether there exists a pathology report, which can be paired with the input operation note. |

TABLE 2-continued

| Gate Function | Description | Example |
|---|---|---|
| CONFIRM[X] | Returns true if a conclusion X has strong confidence and false otherwise. This is able to identify cases where there lacked solid evidence to be sure. | |
| COUNT[X, C] | Count number of X and gives true only if the count result satisfies Condition C. | In [fig], we used COUNT[img, >=2] to show that at least two supportive imaging reports are required to give positive to recurrence. |

After defining the gate functions, decision trees can be created for extracted operation notes and imaging reports for example.

Figure 3:
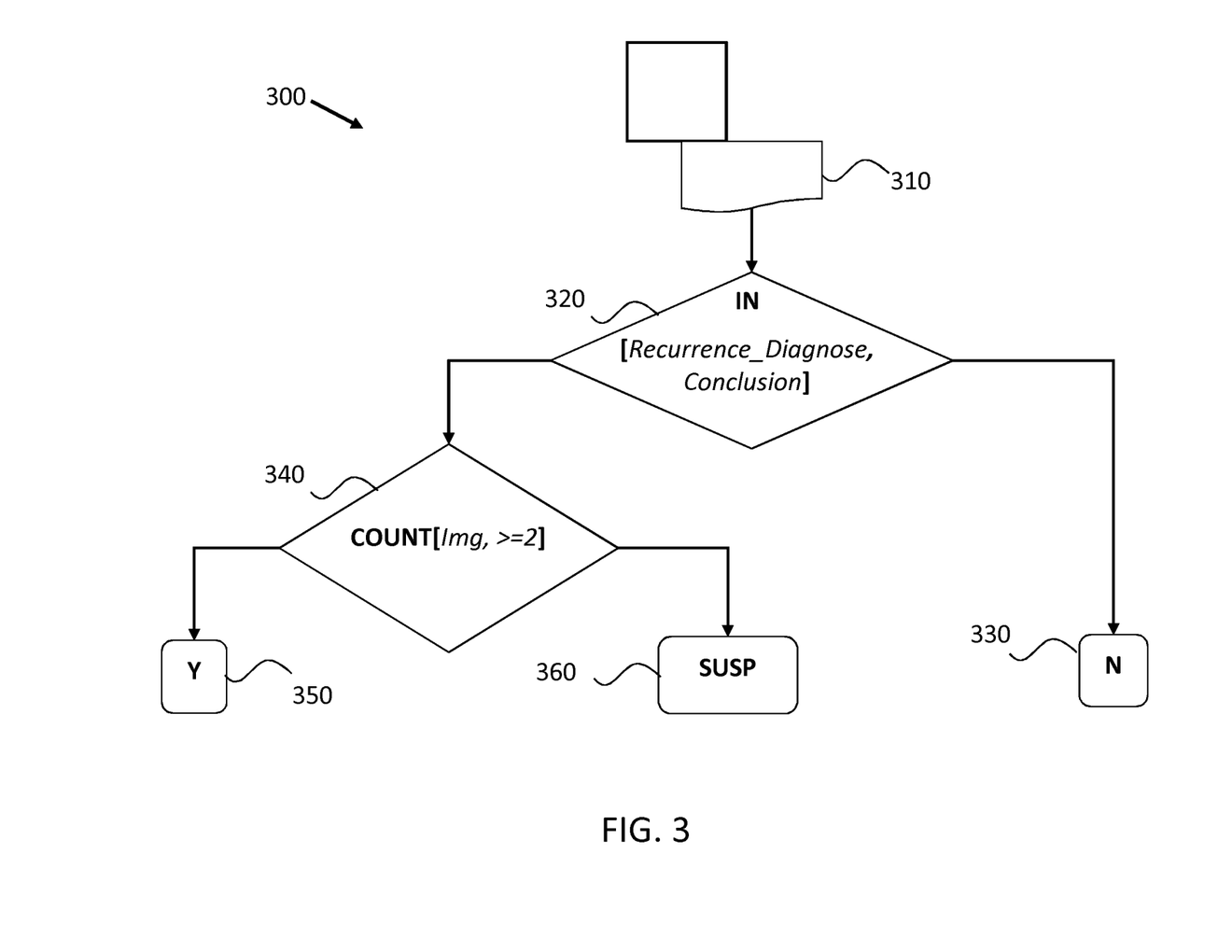
FIG. 3 depicts an exemplary decision tree using phenotypes extracted from imaging reports.

For instance, an exemplary decision tree 300 using phenotypes extracted from imaging reports is illustrated in FIG. 3. The decision tree 300 receives an extracted imaging report 310 and proceeds to step 320 wherein the gate function "IN[Recurrence_Diagnose, Conclusion]" is implemented. This is used to check if a diagnosis of recurrence appears in conclusion part of the imaging report. If the result of the gate function in step 320 is false/negative, a negative decision is provided from leaf 330. If the result of the gate function in step 320 is true/positive, the gate function "COUNT[Img, >=2]" is implemented in step 340. This requires at least two supportive imaging reports in order to proceed to a positive decision from leaf 350 of the decision tree. If the count is only 1, the decision is suspended at leaf 360.

By way of example, such an imaging report decision tree as that of FIG. 3 may be used when operation notes are missing. In such circumstances, it may be that a patient did not receive treatment after an imaging diagnosis was given, but this is still meaningful to know recurrence status. In this case, result is positive if at least two imaging reports have indicated recurrence.

DST Encoder

Decision trees may be implemented and executed using a DST. For instance, to enable fast implementation and simple generalization of M-D processes and decision trees, it is proposed to use DST files to encode everything needed for computation. The atomic building block of DST file may be referred to as a "unit".

Exemplary code grammar for constructing a DST unit is as follows:

"@<item>"|"@<item>#<N>|@<item>==<C>":

and the grammars to acquire value of the item via name-get and define-get are as follows:

```
"<value>"                                #define-get by assigning a value
"<name>::<type>"                         #name-get as type
|{"item.ATTR": "<value> | "&<function_name>", ...}   #define-get
by defining attributes
|{<DST_unit>}                            #define-get by nested DST unit
| "&<function_name>"                     #name-get by specifying a defined
                                         function
"&<DST_unit_name>"                       #name-get by specifying a defined
                                         unit
```

Here, it is noted that "#<N>" assigns a sequence number to the item, and "==<C>" indicates a conditional item where condition C is satisfied.

Inside a DST unit, elements starting with a "@" symbol denote data items to be acquired, either by naming it or by defining it. Data items are built-in types and mainly include name, phenotype, document, logic and return, each serving different purpose. The Meaning of each item type as well as grammars to construct them are listed below as follows:

```
"@name" : "<value>"                      #define name for a DST unit
"@ phenotype":                           #phenotypes
    "<value>"                            # direct assign a value to a phenotype
    "<name>::<type>"                     #name-get from FHIR QR
    |{"item.ATTR": "<value> | "&<function_name>", ...}   #define-get by
defining attributes
"@logic":                                #algorithm that drives decision
    "&<function_name>"                   #name-get by specifying existing function
    |{"item.ATTR": "<value> | "&<function_name>", ...}   #define-get by
defining attributes
"@return" | "@return=<name>" | "@ return==<value>":   #return/conditional return
    {<DST_unit>}                         #define-get by nested DST unit
    | "&<function_name>"                 #name-get by specifying existing function
    | "&<DST_unit_name>"                 #name-get by specifying existing unit
```

Enabler DST

An example of defining enabler DSTs to realize the M-D process is provide as follows.

Firstly, there is implemented a M-phase with a DST unit named MATCH. Then, a D-phase is implemented via a FILTER DST and decision DSTs. Exemplary code is as follows:

```
{
"@name": "MATCH"
"@phenotype": "patient_id:: integer"
"@document#1": {
    "document.NAME": "IMAGE_REPORT"
    "document.QUERY": "fhir_db.qr.find(type=image_report,
        id=patient_id)"
},
```

```
"@document#2": {
    "document.NAME": "OPERATION_NOTE",
    "document.QUERY": " fhir_db.qr.find(type=operation_note,
        id=patient_id) ",
},
"@logic": {
    "logic.name ": "MATCHING Algorithm"
    "logic.DEF": "
    # following is an algorithm that matches operation note with
    imaging reports
    foreach note, report in { @OPERATION_NOTE,
    @IMAGE_REPORT}:
        if &MATCHING({@document#1: note, @document#2:
        report}): ...
        else: ...
        ...
        return pairs
    "
},
```

The above exemplary code demonstrates an implementation of a MATCH operator. The MATCHING function takes two QR documents as an input (e.g. operation notes and imaging report) and is invoked inside "logic.DEF".

Here, it is noted that the exemplary algorithm implementation detailed above uses pseudo code and is not necessarily optimized for conciseness. In reality, users may choose their preferred programing language(s) supported by the framework. Thus, the exemplary code is simply provided to demonstrate how proposed embodiments may be intuitive and provide flexibility when implementing complex processes of a recurrence detection task The helper DST unit MATCHING is then defined. For example, an exemplary implementation of MATCHING in a helper DST is as follows (wherein MT stands for malignant tumor, which is usually mentioned in an imaging report to indicate potential recurrence status):

```
{
    "@name": "MATCHING",
    "@document#1": "operation_note",
    "@document#2": "imaging_report",
    "@phenotype#1": "tumor_number::integer",
    "@phenotype#2": "tumor_position::string",
    "@phenotype#3": "imaging_position::string",
    "@phenotype#4": "MT::boolean",
    "@phenotype#5": "imaging_time::timestamp",
    "@phenotype#6": "operation_time::timestamp",
    "@logic": {
        "logic.name": "MATCHING each pair"
        "logic.DEF": "
            if @MT and @tumor_number > 0 and
                @tumor_position equals @imaging position and
                    @operation_time – @imaging_time <= 1 month:
                return <imaging_report, operation_note>
                else: return NULL
        "
    },
    "@return": "&logic"
}
```

Inside MATCHING, input documents can be obtained via item types "@document#<N>" defined in MATCH. In this exemplary implementation, an operation note is matched to an imaging report if both documents have indicated existence of malignant tumor. In the meantime, the anatomy position in imaging diagnosis must be consistent with that in operation note. A report threshold constraints time distance between two reports should be less than one month, in order to remove two documents that are too far away from each other in time.

Next, implementation of FILTER operator is based on results generated by a MATCH DST. In the proposed framework, this can be achieved by extending MATCH unit directly by creating a FILTER DST unit. By way of example, a piped definition of FILTER operator after invoking MATCH, which is a pre-defined DST unit, is as follows:

```
"&MATCH({"@patient_id": 001})" : {
    "@name": "FILTER"
    "@document": "document_pairs::list",
    "@logic": {
        "logic.name ": "FILTER each pair"
        "logic.DEF": "
            foreach pair in @document_pairs:
                case:           <TYPE_OPRATION_NOTE,
                TYPE_IMAGE_REPORT> return 0
                case: <TYPE_OPERATION_NOTE, NULL>
                return 1
                case: <NULL, IMAGE_REPORT> return 2
        "
    },
    "@return==0=result_case_0": "&decision_case_0({
        @document: pair})",
    "@return==1=result_case_1": "&decision_case_1({
        @document: pair})",
    "@return==2=result_case_2": "&decision_case_2({
        @document: pair})"
```

Exemplary code for another piped definition, which post-processes the results returned by MATCH and FILTER, is as follows.

```
"&MATCH({"@patient_id": 001})" : {
    "&FILTER": {
        "@name": "POST_PROCESSING",
        "@ document#1": "result_case_0",
        "@ document#2": "result_case_1",
        "@ document#3": "result_case_2"
        "@logic": {
            "logic.NAME": "POST_PROCESS algorithm",
            "logic.DEF": "
            # implement how to handle recurrence detection results of
            three cases
            ...
            return results
            "
        }
        "@return=results": "&logic"
    }
}
```

In the example above, patient ID is a phenotype, which is assigned when invoking MATCH. Results returned by MATCH are fetched inside a FILTER unit by assigning the return variable name defined inside MATCH to a document item. In FILTER, conditional return is used to handle the three different cases of filtered document pairs, by invoking corresponding decision DSTs. Each decision DST will be responsible for identifying all recurrence status and time within those filtered document pairs. When both MATCH and FILTER are ready, a pipeline may be used again to create a post-processing DST, which takes output results and wraps them in a way tailored by user.

DST for Decision Tree

A purpose of a decision tree DST is to save users effort in creating a decision process for a recurrence detection task. For data/logic that already exists, it is simply named and retrieved, and, if not, exemplary code for the decision tree of an operation note in DST is as follows:

```
{
    "@name": "DT_OPERATION_NOTE",
    "@phenotype": "operation_type::string",
    "@logic": "&check_operation_type",
    "@return==surgery": {
        "@phenotype": "is_resection::Boolean",
        "@logic": {"logic.DEF", "return @is_resection"}
        "@return==true": {
            "@document":    {"document.NAME":    "PATHOLOGY",
"document.QUERY": "&get_pathology"},
            "@phenotype": "cell_type::string",
            "@logic": {
                "logic.NAME": "check cell type in pathology",
                "logic.DEF": "
                    If not @PATHOLOGY return 2
                    If @cell_type in { HCC, CHC } return 1
                    elif &CONFIRM({ @ henotype:@cell_type}) return −1
                    else return 0
                "
            },
            "@return==1": "Y",
            "@return==−1": "N",
            "@return==0": "SUSP",
            "@return==2": "CHK"
        },
        "@return==false": {
            "@logic":{"logic.DEF": "return@operation_type in {RFA, PEI,
MWA }" },
            "@return==true": {
                "@phenotype#1": "is_open_close_surgery::boolean",
                "@phenotype#2": "tumor_number::integer",
                "@phenotype#3": "is_maglinant_tumor::boolean",
                "@phenotype#4": "is_give_up_resection::boolean",
                "@logic": {
                    "logic.DEF": "
                        If not @is_open_close_surgery return 1
                        elif    not   @is_malignant_tumor   or
@tumor_number==0 return −1
                        elif @is_give_up_resection return 1
                        else return −1
                    "
                },
                "@return==1": "Y",
                "@return==−1": "N"
            },
            "@return==false": "N"
        }
    },
    "@return==intervention": {
        "@phenotype": "tumor_staining::boolean",
        "@ logic": "&existing_tumor_staining",
        "@return==1": "Y",
        "@return==−1": "N",
        "@return==2": "SUSP"
    }
}
```

Finally, this DST is put into a decision case DST and connected to MATCH-FILTER defined above. A missing imaging diagnosis report is a complicated example situation, since it lacks sufficient information to mark a time for recurrence. Normally, admission notes from before a medical operation may be used, wherein an imaging diagnosis history outside the medical facility will normally be recorded in a subject's medical history. With a proposed DST, a user obtain a phenotype by NLP simply by naming it, which is shown in the following example code:

```
"&MATCH({ @patient_id: 001})": {
    "@name": "FILTER",
    ...
    "@return==0=result_case_0": "&decision_case_0({ @document: pair})",
    "@return==1=result_case_1": "&decision_case_1({ @document: pair })",
    "@return==2=result_case_2": "&decision_case_2({ @document: pair })"
}
{
    "@name": "decision_case_2",
    "@document#1": "pair",
    "@document#2": {
        "document.NAME": "operation_note",
        "document.QUERY": "@pair[0]"
    },
```

```
    "@logic": {
        "logic.NAME": "DT_OPN",
        "logic.DEF": "
            return         &DT_OPERATION_NOTE({ @document:
operation_note})=='Y' or 'SUSP'
        "
    },
    "@return==(Y or SUSP)=status": {
        "@name": "MATCH_ADMISSION_NOTE",
        "@logic": {"logic.DEF": " ... return admission_note"},
        "@return=admission_note": {
            "@document": "admission_note",
            "@phenotype": "is_imaging_diagnosis_mentioned",
            "@logic": {"logic.DEF": "return is_imaging_diagnosis_mentioned"},
            "@return=true": "&MARK({ @phenotype: status, @document:
admission_note})",
            "@return=false": "&MARK({ @phenotype: status, @document:
operation_note})"
        }
    }
}
```

The exemplary code above provides an example DST of a decision case, wherein an imaging diagnostic report is missing. It takes filtered paired documents from MATCH-FILTER DST and computes the result by invoking decision DST for operation notes.

DST Execution

Here, an exemplary execution process is summarized, assuming that all information required was extracted by NLP and stored as FHIR questionnaire response resource. During execution, enabler DSTs and decision DSTs are first converted into executable codes by a processor. For this, the processor will parse DST files, linking them together, and convert them into executable codes. After that, the processor handles everything for users at run-time, e.g. getting phenotypes via FHIR query interface, executing codes implemented by users, and return final results.

Accordingly, it will be appreciated that execution or implementation of proposed embodiment may provide for the retrieval of clinical data, and this may then be leveraged for the purpose of detecting the recurrence of a medical condition in a clinical context. Proposed concepts may therefore provide a method for detecting recurrence of a medical condition which employs NLP for the extraction of data and the use of a standardized model to reformulate the extracted data into structured data that facilitates data retrieval.

Embodiments may therefore be employed as a component for recurrent detection on a timeline of subject (e.g. medical patient). Such embodiments may improve both efficiency and performance of machine-aided recurrence detection process under the trend of increasing amount of clinical research data. Proposed concepts may also help to provide strong generalizability. Although embodiments may be particularly beneficial for detecting the recurrence of various types of cancer, it will be understood the proposed concepts and embodiments may be useful for detecting the recurrence of a broad range of medical conditions.

Figure 4:
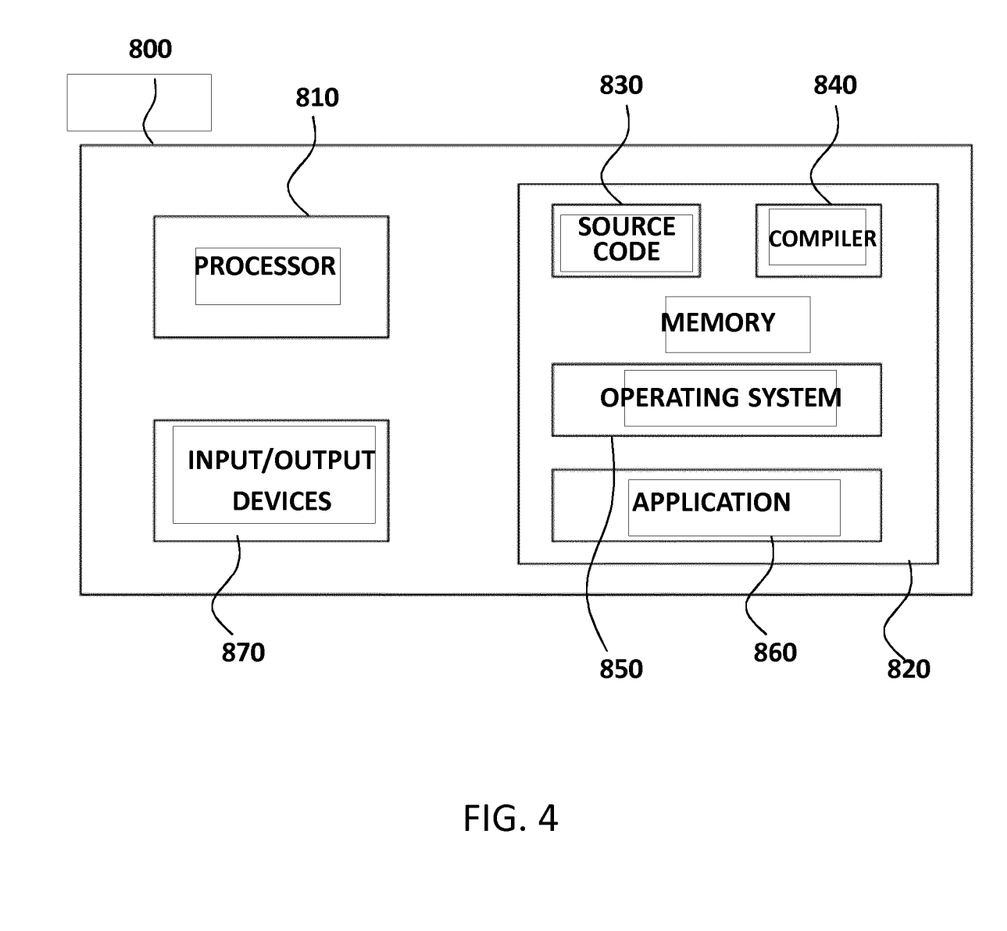
FIG. 4 is a simplified block diagram of a computer within which one or more parts of an embodiment may be employed.

FIG. 4 illustrates an example of a computer 800 within which one or more parts of an embodiment may be employed. Various operations discussed above may utilize the capabilities of the computer 800. For example, one or more parts of a system for providing patient-specific information (or display unit thereof) may be incorporated in any element, module, application, and/or component discussed herein.

The computer 800 includes, but is not limited to, PCs, workstations, laptops, PDAs, palm devices, servers, storages, and the like. Generally, in terms of hardware architecture, the computer 800 may include one or more processors 810, memory 820, and one or more I/O devices 870 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 810 is a hardware device for executing software that can be stored in the memory 820. The processor 810 can be virtually any custom made or commercially available processor, a central processing unit (CPU), a digital signal processor (DSP), or an auxiliary processor among several processors associated with the computer 800, and the processor 810 may be a semiconductor based microprocessor (in the form of a microchip) or a microprocessor.

The memory 820 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 820 may incorporate electronic, magnetic, optical, and/or other types of storage media. Note that the memory 820 can have a distributed architecture, where various components are situated remote from one another, but can be accessed by the processor 810.

The software in the memory 820 may include one or more separate programs, each of which comprises an ordered listing of executable instructions for implementing logical functions. The software in the memory 820 includes a suitable operating system (O/S) 850, compiler 840, source code 830, and one or more applications 860 in accordance with exemplary embodiments. As illustrated, the application 860 comprises numerous functional components for implementing the features and operations of the exemplary embodiments. The application 860 of the computer 800 may represent various applications, computational units, logic, functional units, processes, operations, virtual entities, and/or modules in accordance with exemplary embodiments, but the application 860 is not meant to be a limitation.

The operating system 850 controls the execution of other computer programs, and provides scheduling, input-output control, file and data management, memory management, and communication control and related services. It is contemplated by the inventors that the application 860 for implementing exemplary embodiments may be applicable on all commercially available operating systems.

Application 860 may be a source program, executable program (object code), script, or any other entity comprising a set of instructions to be performed. When a source program, then the program is usually translated via a compiler (such as the compiler 840), assembler, interpreter, or the like, which may or may not be included within the memory 820, so as to operate properly in connection with the O/S 850. Furthermore, the application 860 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 870 may include input devices such as, for example but not limited to, a mouse, keyboard, scanner, microphone, camera, etc. Furthermore, the I/O devices 870 may also include output devices, for example but not limited to a printer, display, etc. Finally, the I/O devices 870 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 870 also include components for communicating over various networks, such as the Internet or intranet.

If the computer 800 is a PC, workstation, intelligent device or the like, the software in the memory 820 may further include a basic input output system (BIOS) (omitted for simplicity). The BIOS is a set of essential software routines that initialize and test hardware at startup, start the O/S 850, and support the transfer of data among the hardware devices. The BIOS is stored in some type of read-only-memory, such as ROM, PROM, EPROM, EEPROM or the like, so that the BIOS can be executed when the computer 800 is activated.

When the computer 800 is in operation, the processor 810 is configured to execute software stored within the memory 820, to communicate data to and from the memory 820, and to generally control operations of the computer 800 pursuant to the software. The application 860 and the O/S 850 are read, in whole or in part, by the processor 810, perhaps buffered within the processor 810, and then executed.

When the application 860 is implemented in software it should be noted that the application 860 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 860 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The description has been presented for purposes of illustration and description, and is not intended to be exhaustive or limited to the invention in the form disclosed. Many modifications and variations will be apparent to those of ordinary skill in the art. Embodiments have been chosen and described in order to best explain principles of proposed embodiments, practical application(s), and to enable others of ordinary skill in the art to understand various embodiments with various modifications are contemplated.

The invention claimed is:

1. A method for detecting a recurrence of a medical condition in a subject previously treated for the medical condition by executing a plurality of machine-readable instructions of a non-transitory machine-readable medium, the method comprising:

receiving a first data set comprising first information of a first type relating to the medical condition of the subject corresponding to a first treatment;

receiving a second data set comprising second information relating to the medical condition of the subject corresponding to a second treatment, the second information being of a second updated type different from the first type;

generating, by a plurality of natural language processing (NLP) modules, a list of phenotypes from the first data set and the second data set;

extracting the first information from the first data set, by a first NLP module of the plurality of NLP modules;

extracting the second information from the second data set, by a second NLP module of the plurality of NLP modules;

reformulating, using a resource wrapper interface, the first information and the second information into structured data based on a standardized model and the list of phenotypes;

obtaining, from a user, a data retrieval request comprising a structured query adhering to a template and including a new phenotype, such that the new phenotype is received directly from the user within the structured query;

in response to obtaining the data retrieval request, automatically identifying the recurrence of the medical condition in the first information of the first type and the second information of the second updated type, the automatically identifying the recurrence comprising:

determining that the medical condition in the first information of the first type and the second information of the second updated type correspond to the new phenotype;

in response to determining that the medical condition in the first information of the first type and the second information of the second updated type correspond to the new phenotype, creating a domain specific template (DST) function corresponding to the new phenotype;

defining, by the DST function, the new phenotype, wherein the new phenotype is not included within the list of phenotypes generated by the plurality of NLP modules and is defined without receiving an updated list of phenotypes;

matching a first one or more pairs including data elements of the structured data based on the structured query, wherein each of the pair corresponds to the new phenotype, wherein at least one pair of the first one or more pairs includes a null entry corresponding to a missing data element in the structured data;

filtering the first one or more pairs to remove the at least one pair including the null entry, thereby resulting in a second one or more pairs, each pair of the second one or more pairs including two causally connected data elements from the structured data;

determining, by the DST function, the recurrence of the medical condition based on a pair in the second one or more pairs corresponding to the new phenotype, wherein the DST function comprises a decision tree;

marking the determined recurrence with a timestamp associated with at least one of the data elements in the pair; and retrieving at least one of the pair of connected data elements in the second one or more pairs from the structured data in response to identifying the recurrence; and providing, to a display, an output associated with the at least one of the connected data elements retrieved from the structured data, the result from determining the recurrence of the medical condition in the subject, and the timestamp.

2. The method of claim 1, wherein the step of reformulating the first information and second information into structured data comprises:
organizing the extracted information based on a questionnaire format and a format of the extracted information.

3. The method of claim 1, wherein the step of reformulating the first information and second information into structured data comprises:
using the resource wrapper interface to transform the extracted information to a standardized data format, wherein the standardized data format is defined by the standardized model.

4. The method of claim 3, wherein the resource wrapper interface comprises a Fast Healthcare Interoperability Resources (FHIR) resource wrapper interface, and wherein the standardized model comprises a FHIR model.

5. The method of claim 1, wherein the template comprises a definition of permissible phenotypes and decision logic.

6. The method of claim 1, wherein the structured query comprises at least one of: an identifier of a subject; an identifier of a document; a phenotype; a definition of a permissible phenotype; a decision rule; or an identifier of a function.

7. The method of claim 1, wherein the first data set and the second data set comprise unstructured or semi-structured data.

8. The method of claim 1, further comprising receiving a user input identifying the new phenotype.

9. A system comprising at least one processor configured to execute the plurality of machine-readable instructions of claim 1.

10. A system for detecting a recurrence of a medical condition in a subject previously treated for the medical condition, the system comprising:
a non-transitory machine-readable medium comprising a plurality of machine-readable instructions; and
a processor configured to execute the plurality of machine-readable instructions to provide:
a natural language processing arrangement comprising a plurality of natural language processing (NLP) modules adapted to:
receive a first data set comprising first information of a first type relating to the medical condition of the subject corresponding to a first treatment;
receive a second data set comprising second information relating to the medical condition of the subject corresponding to a second treatment, the second information being of a second updated type different from the first type;
generate a list of phenotypes from the first data set and the second data set;
extract the first information from the first data set; and
extract the second information from the second data set;
a first interface component adapted to reformulate the first information and the second information into structured data based on a standardized model and the list of phenotypes;
a second interface component adapted to obtain a data retrieval request comprising a structured query adhering to a template and including a new phenotype, wherein the data retrieval request is provided by a user and the new phenotype is received directly from the user within the structured query;
a data retrieval component adapted to retrieve data from the structured data based on the structured query of the data retrieval request, wherein, in response to obtaining the data retrieval request, the data retrieval component is adapted to automatically identify the recurrence of the medical condition in the first information of the first type and the second information of the second updated type, wherein to identify the recurrence, the data retrieval component is further adapted to:
determine that the medical condition in the first information of the first type and the second information of the second updated type correspond to the new phenotype;
in response to determining that the medical condition in the first information of the first type and the second information of the second updated type correspond to the new phenotype, create a domain specific template (DST) function corresponding to the new phenotype;
define, by the DST function, the new phenotype, wherein the new phenotype is not included within the list of phenotypes generated by the plurality of NLP modules and is defined without receiving an updated list of phenotypes;
match a first one or more pairs including data elements of the structured data based on the structured query, wherein each of the pair corresponds to the new phenotype, wherein at least one pair of the first one or more pairs includes a null entry corresponding to a missing data element in the structured data;
filter the first one or more pairs to remove the at least one pair including the null entry, thereby resulting in a second one or more pairs, each pair of the second one or more pairs including two causally connected data elements from the structured data determine, by the DST function, the recurrence of the medical condition based on a pair in the second one or more pairs corresponding to the new phenotype, wherein the DST function comprises a decision tree;

mark the determined recurrence with a timestamp associated with at least one of the data elements in the pair; and retrieve at least one of the pair of connected data elements in the second one or more pairs from the structured data in response to identifying the recurrence; and an output component adapted to provide, to a display, an output associated with the at least one of the connected data elements retrieved from the structured data, the result from determining the recurrence of the medical condition in the subject, and the timestamp.

11. The system of claim 10, wherein the first interface comprises a resource wrapper interface adapted to transform the extracted information to a standardized data format, wherein the standardized data format is defined by the standardized model.

12. The system of claim 11, wherein the resource wrapper interface comprises a Fast Healthcare Interoperability Resources (FHIR) resource wrapper interface, and wherein the standardized model comprises a FHIR model.

13. The system of claim 10, wherein the template comprises a definition of permissible phenotypes and decision logic.

* * * * *